United States Patent [19]
Rosback

[11] 3,943,183
[45] Mar. 9, 1976

[54] AROMATIC HYDROCARBON ISOMER SEPARATION PROCESS BY ADSORPTION

[75] Inventor: Donald H. Rosback, Elmhurst, Ill.

[73] Assignee: Universal Oil Products Company, Des Plaines, Ill.

[22] Filed: July 31, 1974

[21] Appl. No.: 493,376

Related U.S. Application Data

[60] Division of Ser. No. 401,783, Sept. 28, 1973, Pat. No. 3,878,129, which is a continuation-in-part of Ser. No. 356,666, May 2, 1973, Pat. No. 3,878,127.

[52] U.S. Cl. .................... 260/674 SA; 208/310 Z
[51] Int. Cl.² ............................................ C07C 7/13
[58] Field of Search.... 260/674 SA; 208/310, 310 Z

[56] References Cited
UNITED STATES PATENTS

| | | | |
|---|---|---|---|
| 3,558,730 | 1/1971 | Neuzil | 260/674 |
| 3,636,121 | 1/1972 | Stine et al. | 260/674 |
| 3,686,343 | 8/1972 | Bearden et al. | 260/674 |

Primary Examiner—Delbert E. Gantz
Assistant Examiner—C. E. Spresser
Attorney, Agent, or Firm—James R. Hoatson, Jr.; Thomas K. McBride; William H. Page, II

[57] ABSTRACT

A process for separating the para-isomer from a feed mixture containing at least two bi-alkyl substituted monocyclis aromatic isomers, including the para isomer, said isomers having from 8 to about 18 carbon atoms per molecule which process comprises contacting said mixture with an adsorbent prepared by the steps of: contacting a base material comprising type X or type Y zeolite with a fluoride-containing aqueous sodium hydroxide solution at first ion exchange conditions to effect the addition of sodium to and the extraction of alumina from said base material; treating the sodium-exchanged base material at second ion exchange conditions to effect the essentially complete exchange of sodium cations; and, drying the material at conditions to reduce the LOI at 900° C. to less than about 10 wt. % thereby selectively adsorbing at adsorption conditions said para isomer.

The first ion exchange with a fluoride-containing aqueous sodium hydroxide solution prior to the second ion exchange with a selected cation or cations produces a superior adsorbent for separating the para isomer from a feed mixture comprising at least two bi-alkyl substituted monocyclic aromatic isomers, including the para isomer, the isomers having from 8 to about 18 carbon atoms per molecule. The adsorbent so produced has faster para isomer transfer rates and higher aromatic capacity than one produced either from untreated base material or from base material treated with fluoride or caustic alone. Additionally, a fluoride treatment of base material alone or in combination with or subsequent to a caustic treatment, prior to potassium and barium or barium ion exchange, essentially eliminates a troublesome dustiness characteristic of adsorbents prepared from untreated base material.

9 Claims, No Drawings

3,943,183

AROMATIC HYDROCARBON ISOMER SEPARATION PROCESS BY ADSORPTION

RELATED APPLICATIONS

This application is a division of my copending application Ser. No. 401,783 filed Sept. 28, 1973, now U.S. Pat. No. 3,878,129, Apr. 15, 1975, which is a continuation-in-part application of copending application Ser. No. 356,666, filed May 2, 1973, now U.S. Pat. No. 3,878,127, Apr. 15, 1975.

BACKGROUND OF THE INVENTION

1. Field of the Invention

The fields of art to which this invention pertains are crystalline aluminosilicate adsorbent production and aromatic hydrocarbon isomer separation. More specifically, this application relates to a process for separating the para-isomer from a feed mixture comprising at least two bi-alkyl substituted monocyclic aromatic isomers, including the para-isomer, said isomers having from 8 to about 18 carbon atoms per molecule which process employs a particular crystalline aluminosilicate adsorbent.

2. Description of the Prior Art

There are numerous methods for the manufacture and ionexchange of various crystalline aluminosilicates, particularly the type X and type Y crystalline aluminosilicates, to yield products useful for effecting given hydrocarbon reactions or separations. My invention embodies both a manufacturing method for producing an adsorbent material having superior properties for aromatic hydrocarbon isomer separation and a process for the separation of the para-isomer from a feed mixture comprising at least two bi-alkyl substituted monocyclic aromatic isomers, including the para-isomer, the isomers having from 8 to 18 carbon atoms per molecule which process employes the particular adsorbent.

A common problem encountered with most adsorbents and many catalysts is dust which can form excessive pressure drop after the adsorbent or catalyst has been loaded into the adsorbent chambers or reaction vessel and has been used in the particular process. Certainly it is for the reason that adsorbents and catalysts are manufactured to meet certain minimum physical strength requirements and that they are loaded into chambers and vessels with care to avoid breakage. Although operations such as screening can be used to remove most of the interstitial smaller particles and dust, such operations generally fail to remove dust which may coat particles of adsorbent or catalyst of the proper size. This type of dust, apparently held to the particle by electrostatic attraction, may then later be removed by liquid passing through the adsorbent chamber or catalyst vessel and accumulate to form excessive pressure drops.

I have discovered that the troublesome dustiness characteristic of adsorbents is virtually eliminated by a fluoride treatment of the base material. It is thought that the fluoride solublizes the dust by reacting with combined aluminum compounds present in the dust thereby removing the dust from the particles.

I have, additionally, found that an ion-exchange of a base material with a fluoride-containing aqueous solution of sodium hydroxide followed by an ion-exchange with potassium and barium or with barium alone and then a drying step produces an adsorbent with faster transfer rates and higher aromatic capacity than adsorbents produced by either fluoride or caustic treatment alone or with untreated base. Although it is hypothesized that the ion-exchange with aqueous sodium hydroxide replaces non-sodium cations such as H+ or Group II-A cations occupying exchangeable sites within the zeolite and thereby permits higher amounts of barium and potassium or barium alone to be added during a subsequent ion-exchange step, the synergistic result obtained by combining the fluoride treatment with the sodium ion-exchange is neither expected nor understood.

The prior art has neither disclosed nor suggested the method of making this particular adsorbent nor the aromatic hydrocarbon isomer separation process employing the adsorbent.

SUMMARY OF THE INVENTION

It is an object of the present invention to provide a method for the manufacture of a zeolitic adsorbent which method employs a type X or type Y structured zeolite as an intregal component of the finished adsorbent. It is another object of the present invention to provide a method for the manufacture of an adsorbent which has superior properties when used for the separation of para aromatic isomers and in particular for the separation of para-xylene. It is still another object of my invention to provide an adsorptive process for separating the para-isomer from a hydrocarbon feed mixture containing the para-isomer.

In brief summary, my invention is, in one embodiment, a process for separating the para-isomer from a feed mixture comprising at least two bi-alkyl substituted aromatic isomers, including the para-isomer, said isomers having from 8 to about 18 carbon atoms per molecule which method comprises the steps of: (a) contacting a base material containing type X or type Y zeolite with a fluoride-containing solution of sodium hydroxide solution at first ion-exchange conditions to effect the addition of sodium cations to and the extraction of alumina from the base material; (b) ion-exchanging the base material at second ion-exchange conditions to effect the essentially complete exchange of sodium cations; and, (c) drying the resulting exchanged mass at conditions to reduce the LOI at 900° C. to less than about 10 wt. %, thereby selectively adsorbing at adsorption conditions said para-isomer.

DESCRIPTION OF THE INVENTION

The type X and type Y crystalline aluminosilicates or zeolites herein contemplated are described as a three-dimensional network of fundamental structural units consisting of silicon-centered $SiO_4$ and aluminumcentered $AlO_4$ tetrahedra interconnected by a mutual sharing of apical oxygen atoms. The space between the tetrahedra is occupied by water molecules and subsequent dehydration or partial dehydration results in a crystal structure interlaced with channels of molecular dimension.

The type X structured and type Y structured zeolite as used in this specification shall include crystalline aluminosilicates having such three dimensional interconnected structures and as specifically defined by U.S. Pat. Nos. 2,882,244 and 3,130,007. The terms "type X structured" and "type Y structured" zeolites shall include all zeolites which have a general structures as represented in the above cited patents.

The type X structured zeolite in the hydrated or partially hydrated form has the general empirical formula as shown in Formula 1 below:

Formula 1

$$(0.9\pm0.2)M_{2/n}O:Al_2O_3:(2.5\pm0.5)SiO_2:yH_2O$$

where M represents at least one cation having a valence of not more than 3, $n$ represents the valence of M and $y$ is a value up to about 8, depending upon the identity of M and the degree of hydration of the crystal. The cation M may be one or more of a number of cations such as the hydrogen cation, the alkali metal cation, or the alkaline earth cations or other selected cations and is generally referred to as an exchangeable site.

The type Y structured zeolite in the hydrated or partially hydrated form can be represented in terms of the mole oxides for the sodium form as represented by Formula 2 below:

Formula 2

$$(0.9\pm0.2)Na_2O:Al_2O_3:wSiO_2:yH_2O$$

where $w$ is a value of greater than about 3 up to 8, and $y$ may be any value up to about 9.

The term "type X zeolite" and "type Y zeolite" as employed herein shall refer not only to type X structured and type Y structured zeolites containing sodium cations but to those containing other cations such as the hydrogen cations, the alkali metal cations or the alkaline earth cations. Typically both the type X and type Y structured zeolites as initially prepared are predominantly in the sodium form but they may contain, possibly as impurities, the other cations as mentioned above.

The term "base material" as used herein shall refer to a type X or type Y zeolite-containing starting material used to make final adsorbent by the method of this invention. Usually such base material will be predominantly in the sodium form of the zeolite. Generally the base material will be in the form of particles such as extrudates, aggregates, tablets, pills, macro-spheres, or granules produced by grinding any of the above to a desired size range. The type X or type Y zeolite can be present in the base material in concentrations generally ranging from about 75 wt. % to about 90 wt. % of the base material based on a volatile free composition. The remaining material in the base material generally comprises amorphous silica or alumina or both which is present in intimate mixture with the zeolite material. This amorphous material may be an adjunct of the manufacturing process of the type X or type Y zeolite (for example, intentionally incomplete purification of the zeolite during its manufacture) or it may be added to the relatively pure zeolite to aid in forming particles of the zeolite.

A specific base material is commercially available nominal 1/16-inch extrudate comprising 13X zeolite and a minor amount of amorphous material as binder. This base material is primarily in the sodium form; that is, the cation represented as M in Formula 2 above is primarily sodium. By chemical analysis the $Na_2O/Al_2O_3$ ratio is usually about 0.7 or less and can typically be about 0.6 or less which, it should be noted, is less than the $0.9\pm0.2$ indicated in Formula 1 above. Other cations such as H+ and any of the Group IIA metal cations may be present, primarily as impurities, to supply the remainder of the cations needed for chemical balance. The silica to alumina ratio of this starting material by X-ray determination is about 2.5 and the same ratio by chemical analysis is about 2.6. Normally the starting material whether in the extrudate or pellet form is granulated to a particle size range of about 20–40 mesh (Standard U.S. Mesh) before the first ion exchange step is begun. This is approximately the desired particle size of the finished adsorbent.

The first ion exchange with a fluoride-containing sodium hydroxide solution replaces non-sodium cation impurities in the type X or type Y zeolite contained in the base material thereby converting the zeolite essentially completely to the sodium form. Increasing the sodium content of the zeolite permits a higher loading of barium and potassium cations or of the barium cation alone into the zeolite structure on a subsequent ion exchange. To produce an acceptable adsorbent it is preferred that the sodium content of the starting material, as characterized by the weight ratio $Na_2O/Al_2O_3$ be increased to a ratio greater than about 0.70 and more preferably from about 0.75 to 1.0. Ion exchange conditions should be so regulated to achieve this degree of ion exchange.

Although mild ion exchange conditions are employed, this step additionally removes a small amount of silica and alumina. Total silica and alumina removal from the base material is from about 1 to about 15% and is generally in the range of about 1 to 5 wt. %. Analyses indicate that the bulk of both soluble and insoluble material removed from the base material is aluminum, as alumina or sodium aluminate. At least a portion of the alumina extracted appears to be from the zeolite itself rather than from any amorphous material since there is some nominal loss of zeolite as detected by X-ray analysis after this step. It is not known whether the small amount of silica removed from the base material came from the crystalline (zeolite) portion or the amorphous portion of the base material.

The degree of ion exchange and extraction of alumina achieved is a function of the three variables of caustic and fluoride concentrations, temperature at which the ion exchange is conducted, and the length of time the ion exchange is continued.

The preferred fluoride-containing sodium hydroxide solution employed will be sodium hydroxide and sodium fluoride dissolved in water. Suitable concentrations to obtain the desired ion exchange can be from about 0.5 to 10 wt. % of sodium hydroxide with the preferred concentration being from about 0.5 to 5 wt. % and from about 0.1 wt. % up to the solubility limit (about 5%) of sodium fluoride. By using solutions containing sodium hydroxide and sodium fluoride within these ranges of concentration, the desired ion exchange can be obtained at temperatures from about 50° to 250° F. with temperatures from about 150° to 250° F. being especially preferred. Operating pressure is not critical and need only be sufficient to insure a liquid phase. Operating pressures can range from about atmospheric pressure to about 100 psig. The length of time required for the ion exchange will vary, depending upon the solution concentration and temperature, from about 0.5 to 5 hours. Within the above preferred concentrations and temperature ranges, a contact time which has been shown to be especially preferred is about 2 to 3 hours. Continuous or batch-type operations can be employed. The ion exchange step should be controlled so that the zeolite structure will not be destroyed and so that the final product will have a $Na_2O/Al_2O_3$ ratio greater than about 0.7.

After the first ion exchange step the sodium exchanged particles are treated at second ion-exchange conditions to effect essentially complete exchange of the sodium cations with both barium and potassium cations in a weight ratio of from about 1.5 to 200 or with barium cations alone.

Second ion exchange conditions will include a temperature of from about 50° to about 250° F. and a pH sufficient to preclude the formation of the hydrogen form of the zeolite. The pH will therefore be greater than 7 and preferably within the range of 7 to 10. Operation pressure is not critical and need only be sufficient to insure a liquid phase. Operating pressures can range from about atmospheric pressure to about 150 psig. The length of time for the essentially complete exchange of the sodium cations will be from about 0.5 to about 5 hours depending upon the concentration of the cation in the ion exchange medium and the temperature. The term "essentially complete exchange" as used herein shall mean that the sodium cation content has been reduced to about 2.0 wt. % or less and more preferably to about 1 wt. % or less.

The preferred method of ion-exchange when the adsorbent contains both barium and potassium cations is a two-step procedure wherein the sodium-exchanged particles are initially treated in contact with an aqueous solution of a potassium salt, preferably an aqueous solution of potassium chloride, for a time sufficient to reduce the sodium cations to less than about 2 wt. % of the zeolite and yield the potassium form of the zeolite. The exchange can be either a continuous or a batch type operation. The ion-exchange is suitably accomplished on passing a 7 wt. % aqueous potassium chloride solution through a bed of the sodium-exchanged particles at about 180° F. at a liquid hourly space velocity of about one until a total of approximately 13 pounds of solution per pound of said particles has been passed in contact therewith.

The potassium-exchanged particles can then be washed with water to remove excess ion exchange solution.

The washing medium will be water which has a pH adjusted to and maintained within the range of 7 to 10 by adding small amounts of potassium hydroxide. Since the primary purpose of the sodium cation ion exchange was to remove hydrogen cation (and metal cation) contaminants, this pH range is necessary to avoid redepositing hydrogen cation on the adsorbent mass. Washing temperatures can include temperatures within the range of about 100° to about 200° F. with a temperature of about 100° to 145° F. preferred. Although the washing step can be done in a batch manner, with one aliquot of wash water at a time, the washing step is generally and preferably done on a continuous flow type basis with water passed through a bed of the adsorbent at a given liquid hourly space velocity and a temperature for a period of time in order that from about 1 to about 5 gallons of water per pound of starting material is used to wash the material. Preferred washing conditions include using liquid hourly space velocities from about 0.5 to 5, with 1.5 being preferred, to pass from about 1 to about 3 gallons of wash water per pound of starting material over the ion exchanged adsorbent.

The potassium-exchanged particles are then treated in contact with an aqueous solution of a barium salt in the second step of the two-step ion-exchange procedure to achieve the desired weight ratio of barium to potassium on the finished adsorbent. Preferably an aqueous solution of from about 0.2 to about 5 wt. % barium chloride is recycled through the particle bed at about 180° F. and at a liquid hourly space velocity of from about 1 to about 5 until the desired degree of exchange has been achieved. After the barium-exchange step is completed, the water-washing step is repeated, again maintaining a pH of 7 or greater in order to prevent or minimize the possibility of formation of the hydrogen form of the zeolite. A good indication of complete washing can be made by quantitatively testing the effluent wash water for the presence of the anion portion of the salt used in the ion exchange solution.

The above-mentioned two-step potassium and barium ion-exchange procedure is not necessarily limiting as it has been found possible to employ a single step ion-exchange in which both barium and potassium are placed on the zeolite. However, the two-step procedure allows more precise control of the amount of cations placed on the zeolite.

When it is desired that the sodium cations be essentially completely exchanged with only barium cations, then a procedure like that of the second step of the above described two-step procedure will be used alone to effect the exchange with barium cations. I have found that by the method of this invention a suitable adsorbent can be prepared without the potassium cations.

When the wash step is completed the wet adsorbent particles will usually contain from about 30 to about 50 wt. % volatile matter (water) as measured by loss on ignition to 900° C. In this specification, the volatile matter content of the zeolitic adsorbent is determined by the weight difference obtained before and after drying a sample of adsorbent in a high temperature furnace at 900° C. under an inert purge gas stream such as nitrogen for a period of time sufficient to achieve a constant weight. The difference in weight, calculated as a percentage of the sample's initial weight, is reported as loss on ignition (LOI) at 900° C. and represents the volatile matter present within the adsorbent. The remaining step in the method of manufacture then is the drying step to reduce the LOI at 900° C. to less than about 10 wt. % with the preferred LOI being about 3 to 7 wt. %. After the washing has been completed, the particles can be unloaded and dried in a force air oven at temperatures above the boiling point of water but less than about 500° and preferably about 150° C., for a period of time sufficient to remove enough water so that the volatile matter content of the zeolite is below about 10 wt. %. Other methods of drying may be used which can include drying in the presence of an inert gas or under a vacuum, or both.

The anticipated use for the adsorbent prepared by the method of this invention is in various processes for the separation of the para-isomer from a feed mixture comprising at least two bialkyl substituted monocyclic aromatic isomers, including the paraisomer, said isomers having from 8 to about 18 carbon atoms per molecule. Specifically, my adsorbent is useful for separating the para-xylene from a feed mixture comprising para-xylene and at least one other $C_8$ aromatic isomer.

The particular usefulness of this adsorbent and general insight into its desirable characteristics may be better understood by brief reference to such aromatic isomers and separation processes. Specifically, the feed stocks which can be used in the process of this invention are characterized by the formula shown in Formula 3 below:

Formula 3

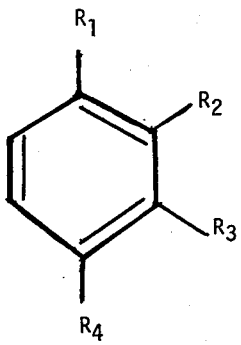

wherein, $R_1$, $R_2$, $R_3$, and $R_4$ are selected from the group of alkyl chains in a manner to allow an essentially bi-alkyl substitution at either ortho-, meta-, or para-isomer positions on the aromatic ring. The R substitution groups up to and including chains having 11 or less carbon atoms per molecule. The alkyl side chains can be both normal and branched in nature and are preferably saturated chains.

Specific representative compounds which can be utilized as feedstocks in the process include those feedstocks containing the xylene isomers and ethylbenzene and the various isomers of methylethylbenzene, diethylbenzene, isopropyltoluene, the methylpropylbenzenes, ethylpropylbenzenes, methybutylbenzenes, ethylbutylbenzene, dipropylbenzenes, methylpentylbenzene, etc., and combinations thereof. The above list only represents a small fraction of compounds whose isomers can be separated by the specific adsorbent produced by the method of this invention.

The isomers of such compounds are separated by this adsorbent according to their configuration depending whether they are of a para-, meta-, or ortho-isomer construction. Specifically, the para-isomer is selectively adsorbed relative to the other isomers. It is contemplated that with feed stocks containing mixtures of more than one class of isomers, for example, $C_8$ isomers in mixture with $C_9$ or $C_{10}$ isomers, molecular weight differences will unduly interfere with selective adsorption based upon isomer configuration differences. It is, therefore, preferred that the process of this invention to employ feed stocks comprising only a single class of aromatic isomers, that is, aromatic isomers having an equal number of carbon number per molecule. It is more preferable to use isomers having as their only differences the location of the alkyl substituted groups in a para-, meta-, or ortho-position. The alkyl structures should preferably be the same for each isomer of a class. In some instances an isomer may have alkyl chains which are both normal or branched or one branched and one normal.

The feed stocks may contain small quantities of straight or branched chain paraffins, cyclo-paraffins or olefinic material. It is preferable to have these quantities at a minimum amount in order to prevent contamination of products from this process by materials which are not selectively adsorbed or separated by the adsorbent. Preferably the above-mentioned contaminants should be less than about 20% of the volume feed stock passed into the process.

To separate the para-isomer contained in the feed mixture, the feed is contacted with a bed or beds of the structured zeolite adsorbent and the para-isomer is selectively retained by the adsorbent while the unadsorbed or raffinate mixture which comprises the other isomers is removed from the interstitial void spaces between the particles or adsorbent and the surface of the adsorbent. The adsorbent is then contacted with a desorbent material which is capable of displacing the adsorbed para-isomer from the adsorbent.

The adsorbent can be contained in a single chamber where through programmed flow into and out of the chamber separation of the para-isomer is effected. A particularly preferred process to use the adsorbent of my invention employs the simulated moving-bed countercurrent operations similar to those disclosed in the pattern of operations in U.S. Pat. No. 2,985,589. The preferred process for separating the para-isomer from a feed mixture containing at least two bi-alkyl substituted monocyclic aromatic isomers, including the para-isomer, said isomers having from 8 to about 18 carbon atoms per molecule comprises the steps of: contacting the feed mixture with the adsorbent at adsorption conditions to effect the selective adsorption of para-isomer by the adsorbent, withdrawing from the bed of adsorbent a raffinate stream comprising less selectively adsorbed aromatic isomers, contacting the adsorbent with a desorbent material at desorption conditions to effect desorption of para-isomer from the adsorbent, and withdrawing a stream containing the para-isomer and desorbent from the adsorbent.

Preferred operating conditions for both adsorption and desorption of this particular process include a temperature within the range of from about 70° to about 450° F. and a pressure within the range of from about atmospheric to about 500 psig. Furthermore, both adsorption and desorption of the para-isomer are effected at conditions selected to maintain liquid phase throughout the bed of adsorbent.

The adsorbent produced by the method of this invention may, of course, be used in other selective adsorption processes for separating aromatic isomers. These might include, for instance, swingbed or moving-bed processes. Adsorption and desorption in such processes may both be conducted in the vapor phase or liquid phase or one operation may be conducted in the vapor phase and the other in the liquid phase. Operating pressures and temperatures for adsorption and desorption might be the same or different.

The desorbents which can be used in the processes employing this adsorbent will vary depending on the type of operation employed. In the swing-bed system in which the selectively adsorbed para-isomer is removed from the adsorbent by a purge stream, gaseous hydrocarbons or other type gases may be used at elevated temperatures or reduced pressures or both to effectively purge adsorbed para-xylene from within the adsorbent. However, in other type operations which are generally operated at substantially constant pressures and temperatures, the desorbent relied upon must be judiciously selected in order that it may displace the adsorbed isomer from the adsorbent without unduly preventing the adsorbed isomer from displacing the desorbent in a following adsorption cycle.

Desorbents which can be used in the process of this invention should also be materials that are easily separable from the feed mixture that is passed into the process. In desorbing the preferentially adsorbed component of the feed, both desorbent and the desorbed feed component are removed from the adsorbent in admixture. Without a method of separation in these two materials, the purity of the selectively adsorbed component of the feed stock would not be very high since it would be diluted with desorbent. It is contemplated that a desorbent having a different boiling range than the feed mixture used should be used in this process. The use of a desorbent of a different boiling range allows a simple separation by fractionation or other methods to removed desired feed components from the desorbent and allow reuse of the desorbent in the process. Specific desorbents which can be used in the process of this invention include benzene, toluene, esters, alcohols, cyclic dienes, the ketones, or a feed component material which has a significantly different boiling range than a boiling range of the feed stock used. It is contemplated that desorbents having both higher and lower boiling points in the feed stock can be utilized. Gaseous materials such as nitrogen, hydrogen, methane, ethane, etc., can also be used as a desorbent materials where the desorbent operation takes place by a purging step.

With the type of processes employing adsorbents to separate aromatic isomers now in mind, one can appreciate that certain characteristics of adsorbents are highly desirable, if not absolutely necessary, to the successful operation of the selective adsorptive process. Among such characteristics are: adsorptive capacity for some volume of the para-isomer per volume of adsorbent; adsorption for the para-isomer with respect to the other aromatic isomers and the desorbent; and sufficiently fast rates of desorption and desoption of the para-isomer to and from the adsorbent. Low or no initial dustiness of the adsorbent and attrition resistance are equally important to avoid possible pressure drop problems after the adsorbent has been loaded.

Capacity of the adsorbent for adsorbing a specific volume of para-isomer is of course a necessity; without such capacity the adsorbent is useless for adsorptive separation. Furthermore, the higher the adsorbent's capacity for the species to be adsorbed, the better is the adsorbent. The increased aromatic capacity of the particular adsorbent produced by the method of this invention makes it possible to reduce the amount of adsorbent needed to separate the desired species contained in a particular rate of hydrocarbon feed mixture. A reduction in the amount of adsorbent required for a specific adsorptive separation reduces the cost of the separation process. It is, of course, important that the good initial capacity of the adsorbent be maintained during actual use in the separation process over some economically desirable life.

The other important adsorbent characteristic is the ability of the adsorbent to separate component of the feed; or, in other words, the selectivity (B), of the adsorbent for one component as compared to another component. Selectivity can be expressed not only for the desired aromatic isomer (para-isomer) as compared to undesired isomers but can also be expressed between any feed stream isomer and the desorbent. The selectivity (B) as used throughout this specification is defined as the ratio of the two components of the adsorbed phase over the ratio of the same two components in the unadsorbed phase at equilibrium conditions.

Selectivity is shown as Equation 1 below:

Equation 1

$$\text{Selectivity} = (B) = \frac{[\text{vol. percent C/vol. percent D}]_A}{[\text{vol. percent C/vol. percent D}]_U}$$

where C and D are two components of the feed represented in volume percent and the subscripts A and U represent the adsorbed and unadsorbed phases respectively. The equilibrium conditions as defined here were determined when the feed passing over a bed of adsorbent did not change composition after contacting the bed of adsorbent. In other words, there was no net transfer of material occurring between the unadsorbed and adsorbed phases.

As can be seen where the selectivity of two components approaches 1.0 there is no preferential adsorption of one component by the adsorbent. As the (B) becomes less than or greater than 1.0, there is a preferential selectivity by the adsorbent of one component. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Desorbents ideally would have a selectivity equal to about 1 or slightly less than 1.

The third important characteristic is the rate of exchange of the adsorbed para-isomer with the desorbent or, in other words, the relative rate of desorption of the para-isomer. This characteristic relates directly to the amount of desorbent that must be employed in the process to recover the adsorbed isomer from the adsorbent. The adsorbent produced by the method of this invention not only has higher aromatic capacity and good selectivity but has faster transfer rates.

The remaining important characteristic, not only for adsorbents but for catalysts as well, is low initial dustiness. This characteristic must of course be coupled with sufficient particle mechanical strength to resist subsequent dust formation during process usage. Such dust, whether present initially or developed later, may migrate within the adsorbent chamber or reaction vessel during process use to form flow restrictions from which excessive pressure drops can result. Such pressure drops grind up adsorbent or catalyst present in the chamber or vessel and can exceed equipment mechanical limitations thereby forcing premature process shutdowns. We have discovered that the dustiness characteristic of adsorbents can be eliminated by a fluoride treatment step in the manufacture of such adsorbents. We would expect that such a step could be incorporated in catalyst manufacturing procedures as well to eliminate the dustiness characteristic of any such catalyst.

In order to test various adsorbents to measure the characteristics of adsorptive capacity, selectivity, and the rate of desorption, a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Attached to the outlet line of the chamber is chromatographic analysis equipment used to analyze the effluent stream leaving the adsorbent chamber.

A pulse test, performed using this apparatus and the following general procedure, is used to determine selectivities and other data for various adsorbent systems. The absorbent was filled to equilibrium with a particular desorbent by passing the desorbent through the adsorbent chamber. At a convenient time, a pulse of feed containing known concentrations of a non-adsorbed paraffinic tracer (n-nonane) and of aromatic isomers all diluted in desorbent is injected for a duration of several minutes. Desorbent flow is resumed, and the tracer and the aromatic isomers are eluted as in a liquid-solid chromatographic operation. The effluent is analyzed by on-stream chromatographic equipment and traces of the envelopes of corresponding component peaks are developed.

From information derived from the chromatographic traces adsorbent performance can be rated in terms of capacity index for the para-isomer, selectivity for the para-isomer with respect to the other isomers and rate of desorption of the para-isomer by the desorbent. The capacity index is characterized by the distance between the center of the para-isomer peak envelope and the $C_9$ tracer peak envelope. It is expressed in terms of the volume in cubic centimeters of desorbent pumped during this time interval. Selectivity, (B), for para-isomer with respect to the other isomers (p/m, p/o) is characterized by the ratio of the distance between the center of the para-isomer peak envelope and the $C_9$ tracer peak envelope to the corresponding distances for the other isomers. The transfer rates are, we have found, best characterized by the widths of the tracer peak envelopes at half intensity. The narrower the peak widths, the faster the transfer rates.

In addition to the para-isomer retention volume derived from the pulse test, total aromatic capacity is also obtained by measuring the volume of a particular para-isomer adsorbed per 70 cc of adsorbent. In this test, the adsorbent is first loaded to equilibrium with a feed blend of known concentrations of aromatic isomers and a tracer component. These are then displaced within a desorbent containing a different para-isomer than that of the feed. The amount of the latter para-isomer adsorbed is termed the total aromatic capacity.

A comparison of the dust content in adsorbents can be made by simply pouring 10 ml. of the adsorbent into 25 ml. of methanol contained in a 25 ± 95 mm 8 dram vial and mixing the contents. The dust will be dispersed in the alcohol and the degree of opacity will serve as an index of the dust content.

To translate pulse test data and total aromatic capacity data into a practical aromatic separation process requires actual testing of the best system in a continuous countercurrent liquid-solid contacting device.

The general operating principles of such a device have been previously described and are found in Broughton U.S. Pat. No. 2,985,589 and a specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are withdrawn through two more. All remaining access lines are inactive and when the position of the distributing valve is advanced by one index all active positions will be advanced by one bed. This simulates a condition in which the absorbent physically moves in a direction countercurrent to the liquid flow. Additional details on adsorbent testing and evaluation may be found in the paper "Separation of $C_8$ Aromatics by Adsorption" by A. J. deRosset, R. W. Neuzil, A. J. Korous, and D. H. Rosback, presented at the American Chemical Society, Los Angeles, Calif., March 28-April 2, 1971.

The superior performance of the adsorbents prepared by the method of this invention which was indicated by the pulse test was confirmed by continuous testing in this device.

EXAMPLE

In this example, four adsorbents were prepared from the same base material and tested to illustrate the desired properties achieved by the method of this invention.

The four adsorbents were prepared from base material comprising commercially available 13X zeolite in the form of nominal 1/16 × ⅛-inch extrudate. This base material was ground to produce 20–40 U.S. Standard Mesh particle size material and divided into four portions from which four adsorbents were prepared.

One portion was simply barium exchanged to produce Adsorbent A. A 190 cc portion of the base material was treated upflow with 28 liters of 0.015 M $BaCl_2 \cdot 2H_2O$ solution at 70° C. and 1.8 liquid hourly space velocity (LHSV). The material was then washed at 70° C. with 2 liters of water over a 2.5 hour period.

A second portion was treated with a solution of NaF only and then barium exchanged to produce Adsorbent B. A 300 cc portion of the base material was batch treated for 3.5 hours at 90° C. with 30 g. NaF dissolved in 600 ml. of deionized water. The material was decant-washed and then barium exchanged in the manner of Adsorbent A.

A third portion was treated with a solution containing both NaF and NaOH and then barium exchanged to produce Adsorbent C. A 200 cc portion of the base material was batch treated for 2 hours at 90° C. with a solution of 25 g. NaF and 20 g. NaOH dissolved in 500 ml. of deionized water. The material was batch washed at 80°–85° C. for 1/2 hour periods with eight 250ml. portions of deionized water and then barium exchanged in the manner described above.

The fourth portion of ground base material was treated with a solution of NaOH only, and then barium exchanged to produce Adsorbent D. A 200 ml. portion of the base material was batch treated for 2 hours at 90° C. with a solution of 20 g. NaOH dissolved in 500 ml. of deionized water. The material was batch washed with water and then barium exchanged.

All four adsorbents were dried for 16 hours at 185° C. with perfluent $N_2$ and then rehydrated to 4 wt. % water prior to being tested for performance by the pulse test previously described.

The testing apparatus was maintained at a controlled temperature of 150° C. with sufficient pressure to ensure liquid phase operations. A desorbent of 30 vol. % para-diethylbenzene and 70 vol. % n-heptane was run through the apparatus at a rate of 1.5 cc per minute. At a convenient time interval the desorbent was stopped and a feed pulse consisting of 5 vol. % para-xylene, meta-xylene, ortho-xylene, ethyl benzene, and n-nonane as a tracer and 75 vol. % desorbent was charged to the adsorbent chamber for a 10-minute interval at 1 LHSV.

From the chromatographic tracers of the envelopes of component peaks, peak envelope widths, para-xylene capacity, and selectivities were determined.

The amount of para-diethylbenzene adsorbed was determined by loading the adsorbent to equilibrium with a feed pulse consisting of 24 vol. % each of the $C_8$ aromatics and 4 vol. % n-nonane tracer and then charging the desorbent of 30 vol. % para-diethylbenzene and 70 vol. % n-heptane to the adsorbent chamber. The amount of para-diethylbenzene adsorbed was then calculated from the breakthrough front of para-diethylbenzene measured from the disappearance of the tracer.

Dust condition of the four adsorbents was determined by the degree of opacity resulting from the simple methanol test previously described.

The results of the testing for the four adsorbents are shown in table 1 below.

Table 1

| Pulse Test and Capacity Data for Adsorbents | | | | |
|---|---|---|---|---|
| Adsorbent | A | B | C | D |
| Treatment | none | NaF | NaF/NaOH | NaOH |
| Wt.% BaO | 30.4 | 31.4 | 35.6 | 32.6 |
| Wt.% Na$_2$O | 1.40 | 1.74 | 1.02 | 1.05 |
| Peak Envelope Widths, cc. for: | | | | |
| n-nonane | 14.5 | 10.1 | 9.9 | 11.5 |
| ethylbenzene (EB) | 20.4 | 15.4 | 15.0 | 19.2 |
| para-xylene (P) | 22.1 | 13.9 | 13.2 | 18.7 |
| meta-xylene (M) | 16.8 | 13.2 | 13.5 | 15.7 |
| ortho-xylene (O) | 16.8 | 12.6 | 13.5 | 15.5 |
| Para-xylene retention volume, cc. | 19.6 | 23.0 | 23.5 | 24.8 |
| Selectivities | | | | |
| P/EB | 1.71 | 1.68 | 1.73 | 1.91 |
| P/M | 3.41 | 3.66 | 3.68 | 5.07 |
| P/O | 2.81 | 3.27 | 3.19 | 4.42 |
| Para-diethylbenzene capacity, cc. per 70 cc adsorbent | 6.38 | 8.00 | 9.75 | 9.15 |
| Dust Condition | dusty | no dust | no dust | dusty |

The higher para-diethylbenzene capacities for Adsorbents C and D indicate that both NaOH/NaF or NaOH treatments confer high total aromatics capacity. The narrowest peak envelope widths for Adsorbent C indicates that the NaOh/NaF treatment confers the fastest para-xylene transfer rates. The table also shows that the best selectivities were obtained with the NaOH treatment alone (Adsorbent D) with next best selectivities obtained with the NaOH/NaF treatment (Adsorbent C). Additionally the table shows that NaF treatment with or without NaOH treatment eliminates dusting (Adsorbents B and C).

The combination of NaOH and NaF treatment renders an adsorbent having the best combination of performance characteristics. This combination is not attainable by either treatment alone and is certainly superior to those of an adsorbent made with neither treatment.

I claim as my invention:

1. A process for separating the para-isomer from a feed mixture comprising at least two bi-alkyl substituted monocyclic aromatic isomers, including the para-isomer, said isomers having from 8 to about 18 carbon atoms per molecule which process comprises contacting said mixture with an adsorbent prepared by the steps of:

a. contacting a base material comprising X or Y zeolite with a fluoride-containing aqueous sodium hydroxide solution at first ion exchange conditions to effect the addition of sodium cations to and the extraction of alumina from said base material;

b. treating the sodium-exchanged base material at second ion exchange conditions to effect the essentially complete exchange of sodium cations with barium or barium and potassium cations; and, c. drying the material at conditions to reduce the LOI at 900° C. to less than about 10 wt. %.

2. The process of claim 1 further characterized in that said para-isomer is para-xylene and said feed mixture comprises para-xylene and at least one other $C_8$ aromatic isomer.

3. The process of claim 1 wherein, in the preparation of said adsorbent, the sodium-exchanged base material is essentially completely exchanged with barium and potassium cations.

4. The process of claim 1 wherein, in the preparation of said adsorbent, the sodium-exchanged base material is essentially completely exchanged with barium cations.

5. The process of claim 1 further characterized in that said adsorption conditions are selected from a temperature within the range of from about 70° to about 450° F. and a pressure within the range of from about atmospheric to about 500 psig. to maintain liquid phase.

6. A process for separating the para-xylene from a feed mixture comprising para-xylene and at least one other $C_8$ aromatic isomer which process comprises the steps of:

a. contacting said mixture with an adsorbent at adsorption conditions to effect the selective adsorption of para-xylene;

b. withdrawing from the adsorbent a stream comprising less selectively adsorbed aromatic isomers;

c. contacting the adsorbent with a desorbent material at desorption conditions to effect desorption of para-xylene from the adsorbent; and, d. withdrawing from the adsorbent a stream containing para-xylene and desorbent;

said adsorbent having been prepared by the steps of:

i. contacting a base material comprising X or Y zeolite with a fluoride-containing aqueous sodium hydroxide solution at first ion exchange conditions to effect the addition of sodium cations to and the extraction of alumina from said base material;

ii. treating the sodium-exchanged base material at second ion exchange conditions to effect the essentially complete exchange of sodium cations with barium or barium and potassium cations; and, iii. drying the material at conditions to reduce the LOI at 900° C. to less than about 10 wt. %.

7. The process of claim 6 further characterized in that said adsorption and desorption conditions are selected from a temperature within the range of from about 70° to about 450° F. and a pressure within the range of from about atmospheric to about 500 psig. to maintain a liquid phase.

8. The process of claim 6 wherein, in the preparation of said adsorbent, the sodium-exchanged base material is essentially completely exchanged with barium and potassium cations.

9. The process of claim 6 wherein, in the preparation of said adsorbent, the sodium-exchanged base material is essentially completely exchanged with barium cations.

* * * * *